(12) United States Patent
Kaneko et al.

(10) Patent No.: US 12,148,127 B2
(45) Date of Patent: Nov. 19, 2024

(54) MEDICAL IMAGE PROCESSING DEVICE, MEDICAL IMAGING APPARATUS, AND NOISE REDUCTION METHOD FOR MEDICAL IMAGE

(71) Applicant: FUJIFILM Healthcare Corporation, Kashiwa (JP)

(72) Inventors: Yukio Kaneko, Chiba (JP); Toru Shirai, Chiba (JP); Atsuro Suzuki, Chiba (JP); Tomoki Amemiya, Chiba (JP); Suguru Yokosawa, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 380 days.

(21) Appl. No.: 17/846,182

(22) Filed: Jun. 22, 2022

(65) Prior Publication Data

US 2022/0414837 A1 Dec. 29, 2022

(30) Foreign Application Priority Data

Jun. 25, 2021 (JP) .................... 2021-106065

(51) Int. Cl.
*G06T 5/70* (2024.01)
*G06T 7/00* (2017.01)
(Continued)

(52) U.S. Cl.
CPC ............. *G06T 5/70* (2024.01); *G06T 7/0012* (2013.01); *G06V 10/22* (2022.01); *G06V 10/50* (2022.01);
(Continued)

(58) Field of Classification Search
CPC ............. G06T 5/70; G06T 7/0012; G06T 2207/10088; G06T 2207/30004;
(Continued)

(56) References Cited

U.S. PATENT DOCUMENTS 6,650,779 B2 * 11/2003 Vachtesvanos ........ G06V 10/52
382/218
10,361,802 B1 * 7/2019 Hoffberg-Borghesani ..................
G06F 3/00
(Continued)

FOREIGN PATENT DOCUMENTS

JP     2004-072422 A      3/2004
JP     2004362074 A  *  12/2004
(Continued)

OTHER PUBLICATIONS

Japanese official action dated Dec. 12, 2023 (and English translation thereof) in Connection with Japanese Patent Application No. 2021-106065.
(Continued)

*Primary Examiner* — Mahendra R Patel
(74) *Attorney, Agent, or Firm* — Paul Teng

(57) ABSTRACT

The invention provides a technique capable of effectively and appropriately removing noise from various kinds of images including noise and artifacts and images in which a noise pattern changes due to a difference in imaging conditions. Based on a noise removal technique using AI, noise characteristics including artifacts are analyzed for each image, the image is classified based on an analysis result, an optimal neural network for a noise processing is applied for each classification, and the noise and the artifacts are reduced.

12 Claims, 13 Drawing Sheets

(51) Int. Cl.
*G06V 10/22* (2022.01)
*G06V 10/50* (2022.01)
*G06V 10/54* (2022.01)
*G06V 10/764* (2022.01)
*G16H 30/20* (2018.01)

(52) U.S. Cl.
CPC ............ *G06V 10/54* (2022.01); *G06V 10/764* (2022.01); *G16H 30/20* (2018.01); *G06T 2207/10088* (2013.01); *G06T 2207/30004* (2013.01); *G06V 2201/03* (2022.01)

(58) Field of Classification Search
CPC ............ G06T 7/41; G06T 2207/30104; G06T 2207/20084; G06T 2207/10081; G06V 10/22; G06V 10/50; G06V 10/54; G06V 10/764; G06V 2201/03; G06V 10/30; G06V 10/82; G16H 30/20; G16H 30/40; A61B 5/7203; A61B 5/055; A61B 5/7217; A61B 5/7253; A61B 5/7257; A61B 5/726; A61B 5/7264; A61B 6/032; A61B 6/5258; A61B 8/5269
USPC ..................................................... 382/131
See application file for complete search history.

(56) References Cited

U.S. PATENT DOCUMENTS

| | | | | |
|---|---|---|---|---|
| 11,625,811 B2* | 4/2023 | Kumar | ................ | G06N 3/08 |
| | | | | 382/276 |
| 11,892,582 B2* | 2/2024 | Gillott | ................ | G01V 1/186 |
| 2004/0027469 A1* | 2/2004 | Tsuruoka | ............ | H04N 25/633 |
| | | | | 348/E5.079 |
| 2005/0254709 A1* | 11/2005 | Geshwind | .............. | G06V 10/56 |
| | | | | 382/182 |
| 2007/0061023 A1* | 3/2007 | Hoffberg | ................ | G06F 3/048 |
| | | | | 348/E5.103 |
| 2013/0064448 A1* | 3/2013 | Tomaselli | ................ | G06T 5/20 |
| | | | | 382/167 |
| 2017/0173262 A1* | 6/2017 | Veltz | ..................... | G16H 20/17 |
| 2019/0095713 A1* | 3/2019 | Leroy | ................... | G06V 10/56 |
| 2020/0118544 A1* | 4/2020 | Lee | ....................... | G10L 15/063 |

FOREIGN PATENT DOCUMENTS

| | | | | | |
|---|---|---|---|---|---|
| JP | 2005017159 A | * | 1/2005 | .......... | G06T 7/0004 |
| JP | 3794505 B2 | * | 7/2006 | .......... | H04N 19/80 |
| JP | 3974946 B2 | * | 9/2007 | .......... | G06K 9/6217 |
| JP | 4167489 B2 | * | 10/2008 | ............ | G08G 1/015 |
| JP | 2013-512024 A | | 4/2013 | | |
| JP | 20188-519861 A | | 7/2018 | | |
| JP | 2018206382 A | * | 12/2018 | ............ | G06N 3/045 |
| JP | 2020-141908 A | | 9/2020 | | |
| WO | WO-2005086890 A2 | * | 9/2005 | ................ | G01J 3/02 |

OTHER PUBLICATIONS

Japanese official action dated Apr. 9, 2024 (and English translation thereof) in connection with Japanese Patent Application No. 2021-106065.

* cited by examiner

MEDICAL IMAGE PROCESSING DEVICE, MEDICAL IMAGING APPARATUS, AND NOISE REDUCTION METHOD FOR MEDICAL IMAGE

BACKGROUND OF THE INVENTION

Technical Field

The present invention relates to an image diagnosis apparatus such as a magnetic resonance imaging (MRI) apparatus or a CT apparatus, and more particularly, to a technique of reducing noise of an image in the image diagnosis apparatus.

Background Art

As an image diagnosis apparatus, a medical imaging apparatus such as a magnetic resonance imaging (MRI) apparatus, a CT apparatus, or an ultrasonic imaging apparatus is widely used. In order to reduce a burden on a subject and increase the number of inspections, high-speed imaging is increasingly necessary. In general, in an imaging apparatus, high-speed imaging can be achieved by reducing the amount of data to be acquired. For example, in an MRI apparatus, various types of high-speed imaging methods such as parallel imaging and compression sensing are proposed in which an echo signal smaller than an echo signal required for an image matrix is measured (under sampled) and is restored by calculation.

However, in the high-speed imaging, there is a problem that noise of an image to be obtained increases, that is, a signal noise ratio (SNR) decreases. This problem is also common to a CT apparatus and an ultrasonic apparatus.

In recent years, research and development for improving image quality using AI have been actively conducted, and a high noise-reduction effect is exhibited. JP-A-2018-206382 discloses an image processing system using a neural network (NN) and proposes that an internal parameter of the NN is adjusted based on data related to an input image, so that noise reduction performance can be improved even when the image has a different amount of noise from an image for learning.

SUMMARY OF THE INVENTION

In an image acquired by the medical imaging apparatus, various types of image quality degradation occur due to an imaging method, an imaging condition, and the like. In particular, when imaging sites, physiques of patients, and the like are different, characteristics of the noise change. For example, in the MRI apparatus, when the imaging condition is determined by adjusting an imaging range or the like in accordance with the patient, characteristics of a spatial distribution of the noise change accordingly. In addition, in accordance with a body shape of the patient, a spatial distribution of sensitivity of signal acquisition is different, and the characteristics of the noise change accordingly. For example, even when adjustment according to a magnitude of the noise is performed as described in JP-A-2018-206382, there is a possibility that an appropriate noise reduction processing cannot be performed unless a processing considering the spatial distribution of the noise is performed, and in this case, another problem such as a blur of the image occurs.

For example, in the MRI apparatus, even when noises of the same noise pattern, for example, Gaussian noise, are mixed in imaging data among a plurality of images taken with different imaging parameters such as a measurement matrix size and a reconstruction matrix size, noise patterns may be different from each other when obtained images are compared, and an appropriate noise may not be obtained even when the obtained images are processed by the same noise reduction method.

An object of the invention is to provide a technique capable of effectively and appropriately removing noise even from an image in which a noise pattern changes due to a difference in imaging parameters.

The invention is based on a noise removal technique using AI, analyzes noise characteristics for each image, classifies images based on an analysis result, and applies an optimum neural network for a noise processing for each classification, thereby reducing noise.

That is, an image diagnosis apparatus of the invention is a medical image processing device that inputs an image acquired by a medical imaging apparatus and outputs an image in which a noise is reduced. The medical imaging apparatus includes: a plurality of processors for noise reduction; an analysis unit configured to analyze a pattern of a signal and noise of the input image and classify the input image; and a processor selection unit configured to select one or a plurality of processors from the plurality of processors based on a classification result of the analysis unit and activate the selected processor.

A noise reduction technique of the invention is a noise reduction method for reducing noise included in an image acquired by a medical imaging apparatus. The noise reduction method includes: analyzing a pattern of the noise of the image and classifying an input image; selecting a predetermined processor from a plurality of processors for noise reduction prepared for each classification based on a classification result of the classification; and executing a noise reduction processing of the input image by the selected processor.

The noise characteristics are mainly determined by a magnitude of the noise and a spatial distribution of the noise, and the pattern of the noise means the magnitude of the noise and the spatial distribution of the noise.

According to the invention, an inappropriate noise reduction processing can be prevented from being performed and an effective noise reduction processing can be implemented by selecting and applying an optimal processor for the noise characteristics of the input image from the plurality of processors prepared in advance in accordance with the noise characteristics.

DESCRIPTION OF EMBODIMENTS

Hereinafter, embodiments of a medical image processing device and a medical imaging apparatus according to the invention will be described.

<Embodiment of Medical Image Processing Device>

Figure 1:
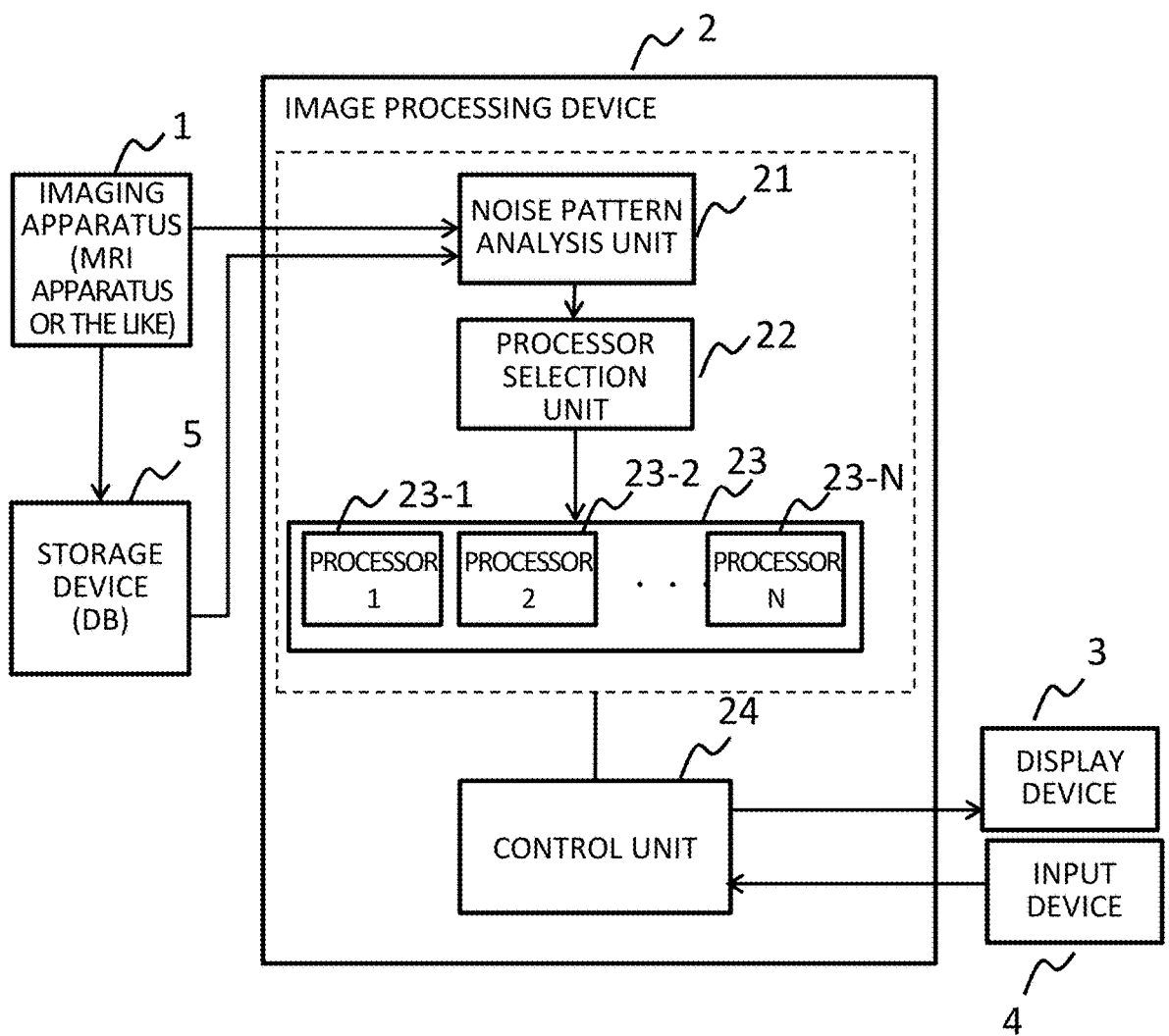
FIG. 1 is a diagram showing an overall configuration of a medical image processing device according to the invention.

FIG. 1 is a diagram showing a configuration example of an embodiment of a medical image processing device. A medical image processing device 2 inputs a medical image acquired by a medical imaging apparatus (hereinafter, also simply referred to as an imaging apparatus) 1 and reduces noise included in the medical image. The medical image processing device 2 includes a plurality of processors 23 learned to perform an optimal noise reduction processing according to a noise characteristic (noise pattern) of the medical image, a noise pattern analysis unit (hereinafter referred to as an analysis unit) 21 configured to input the medical image to be processed from the imaging apparatus 1, analyze a characteristic of the image (input image), and classify the input image into a predetermined pattern, a processor selection unit 22 configured to select a processor corresponding to the pattern classified by the analysis unit 21 from the plurality of processors 23, and a control unit 24 configured to control operations of the analysis unit 21, the processor selection unit 22, and the processors 23.

The medical imaging apparatus 1 is a general medical imaging apparatus such as an MRI apparatus, a CT apparatus, or an ultrasonic imaging apparatus. When the imaging apparatus 1 includes an image processing unit that processes the acquired image, the medical image processing device 2 may function as a part of the image processing unit of the medical imaging apparatus 1, or may be a device independent of the imaging apparatus 1 and connected to the imaging apparatus 1 directly or via a network. In addition, the medical image processing device 2 may also be connected to a storage device 5 such as a medical image database storing a medical image. In that case, the medical image is acquired from the database (storage device 5).

Further, the medical image processing device 2 may include a display device 3 and an input device 4, and can receive a condition or an instruction of a processing by a user via the input device 4 or display a processing result on the display device 3.

The processors 23 includes a plurality of processors 23-1, 23-2, . . . 23-N having different processing contents depending on the noise pattern of the input image to be processed. Each of the processors includes a convolutional neural network (CNN) including an input layer, an intermediate layer, and an output layer. In a processing using such a CNN, by repeating a convolution processing of the image in the intermediate layer, a target high-quality (noise reduced) image is obtained. Optimization of the convolution processing, that is, optimization of a node weight and a convolution coefficient of each layer is performed by data learning. The processors 23-1, 23-2, . . . 23-N learn in advance using a plurality of images having different noise patterns as learning data, and the node weight and the convolution coefficient of each layer are set such that an appropriate noise reduction processing is performed for each noise pattern. In addition, the number of the intermediate layer may also be different for each of the processors.

The analysis unit 21 analyzes and classifies the noise pattern of the input image before a processing by the processors 23. For the analysis, a method for transforming the image into data in a space different from an image space and using a characteristic value in the space and a method regarding a characteristic of the image itself, for example, texture analysis can be used, and these methods may be combined appropriately.

In a learning step of the processors for preparing the plurality of processors 23-1 to 23-N, noises of a large number of images are classified in advance by the same method as the analysis and classification performed by the analysis unit 21 described above, and the learning is performed using a learning data set for each classification. The analysis and classification in the learning step may be performed by the analysis unit 21 of the medical image processing device 2 of the present embodiment, or may be performed by another image processing device having the same configuration as that of the analysis unit 21.

The processor selection unit 22 selects a processor optimal for processing the input image based on an analysis result of the analysis unit 21.

Since the control unit 24 controls an operation of each unit described above, when the processor selection unit 22 selects the predetermined processor 23 for the input image, the control unit 24 controls the operation such that the selected processor 23 processes the input image.

The image processing device 2 is implemented by a computer including a processor such as a central processing unit (CPU) or a graphics processing unit (GPU) and a memory. The CPU reads and executes a program stored in the memory, thereby implementing functions of the processors 23-1 to 23-N, the analysis unit 21, and the processor selection unit 22 by software. A part or all of the processors 23-1 to 23-N, the analysis unit 21, and the processor selection unit 22 may also be implemented by hardware. For example, a circuit design may implement the functions of the processors 23-1 to 23-N, the analysis unit 21, and the processor selection unit using a custom IC such as an application specific integrated circuit (ASIC) or a programmable IC such as a field-programmable gate array (FPGA).

Figure 2:
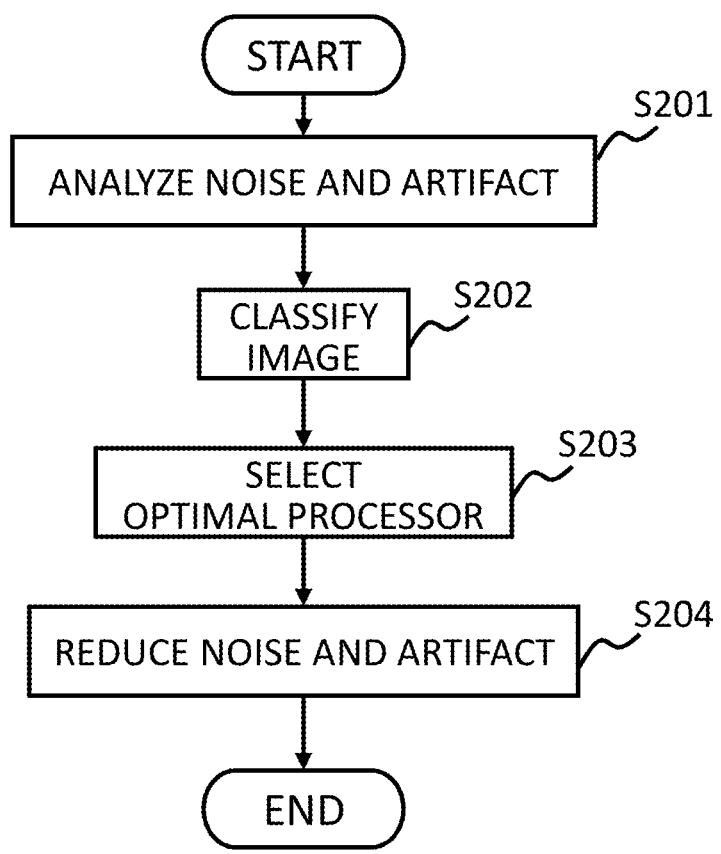
FIG. 2 is a diagram showing an outline of a processing of the medical image processing device of FIG. 1.

An outline of a processing of the medical image processing device 2 having the above configuration is shown in FIG. 2. As shown in the drawing, a basic processing performed by the medical image processing device 2 includes, after inputting an image to be processed (input image), a step S201 of analyzing noise, a step S202 of classifying the image based on the analysis result, a step S203 of selecting the processor optimal for the classified image, and a step S204 of applying the selected processor and reducing the noise.

A processing (learning step) of learning the processors may be a premise of these processings, but the learning step is not necessarily performed by the same medical image processing device 2, and may be performed by another image processing device. However, learning is performed using an image classified by the same method as the analysis method performed by the analysis unit 21 of the medical image processing device 2 as a learning set.

When the medical image processing device 2 includes the display device 3, the image after noise reduction may be displayed on the display device 3, or may be transferred to the imaging apparatus 1 and displayed on a display device of the imaging apparatus 1.

Based on the outline of the configuration and the processing of the medical image processing device 2 described above, a specific embodiment of the processing will be described below.

Embodiment

In the present embodiment, a processing in which an image is acquired by the MRI apparatus and the pattern of the noise mainly differs depending on a size of a measurement matrix will be described.

[Learning of Processors]

Figure 3:
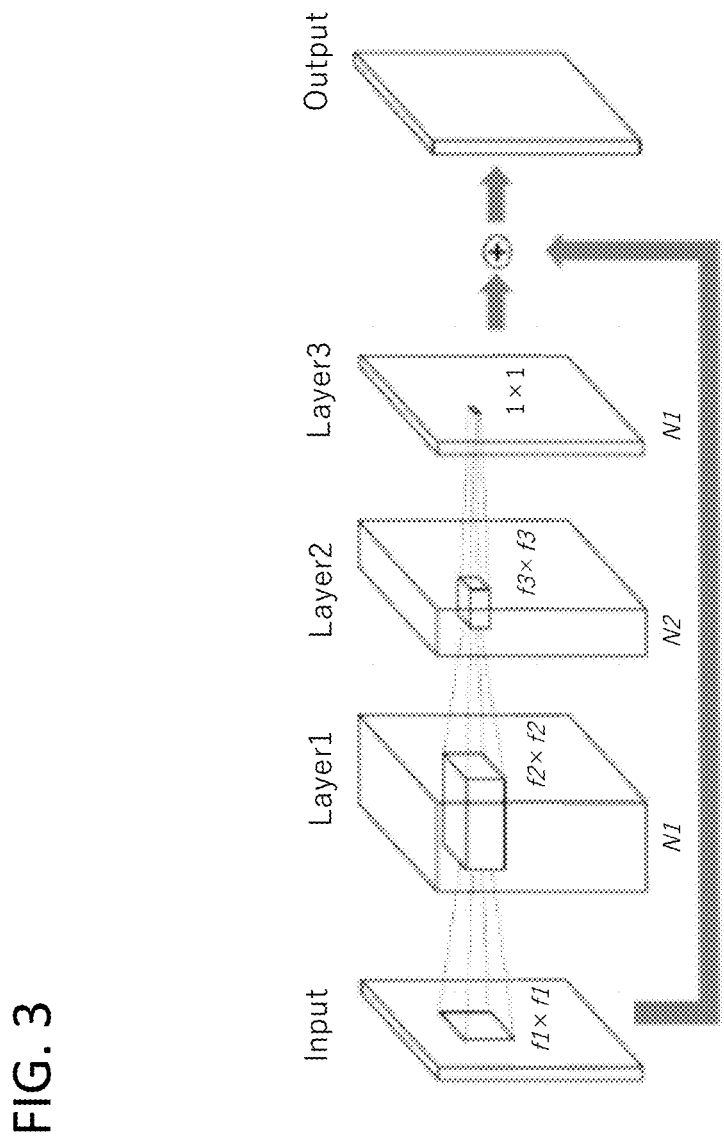
FIG. 3 is a diagram showing a configuration example of a processor.

The learning of the processors 23 is performed to prepare each of the processors 23-1 to 23-N, which are learning models. FIG. 3 shows an example of the convolutional neural network (CNN) constituting the processor. In the drawing, in an example of a super resolution CNN (SRCNN), f1 to f3 in the drawing are kernel sizes of the intermediate layers, and N1 to N3 are depths of the layers. Although a kernel size and a kernel coefficient (convolution coefficient) are optimized by the learning based on a structure of the CNN, the number of layers, the depth, and the like may be further changed.

Figure 4:
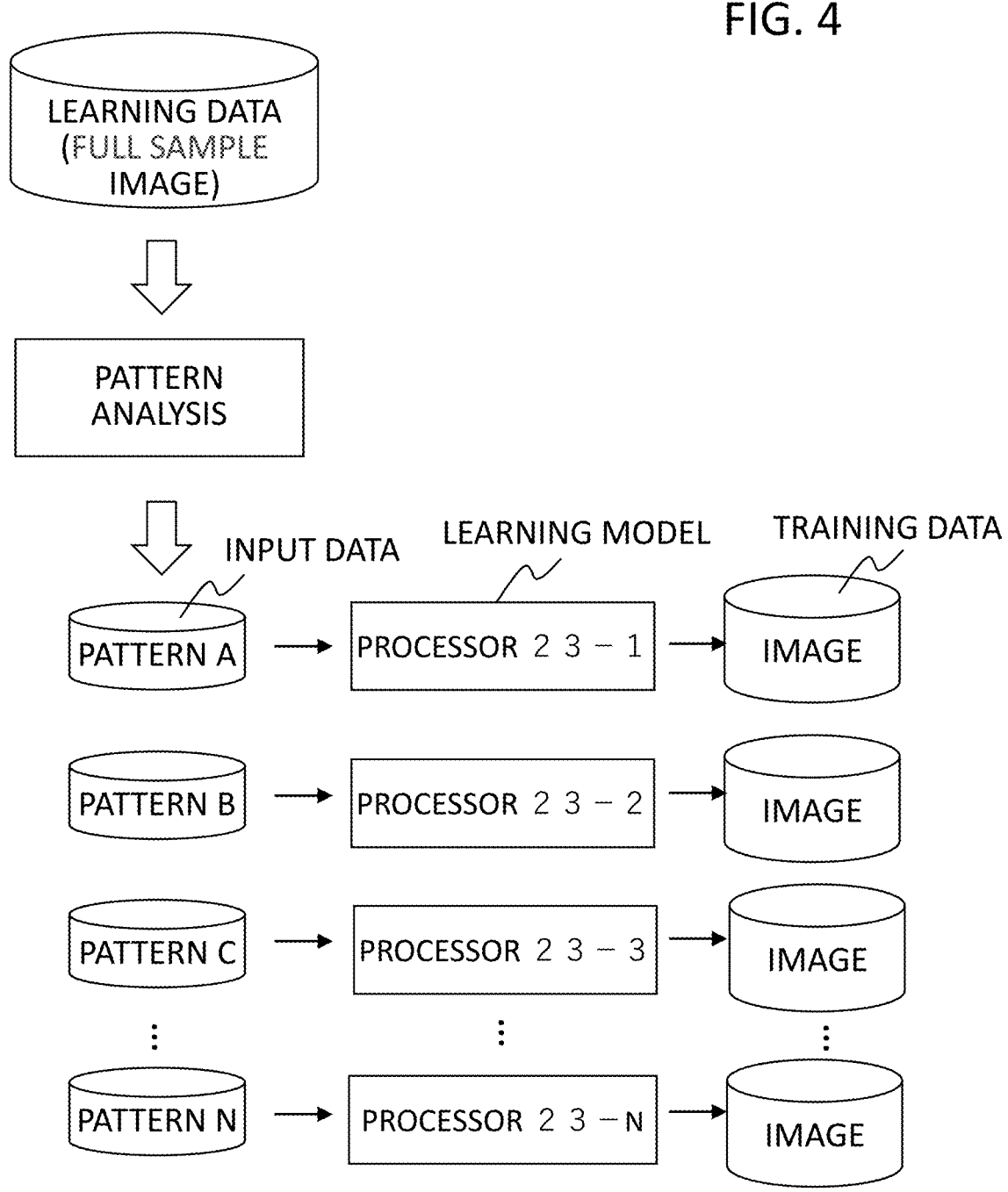
FIG. 4 is a diagram showing a learning step of a plurality of processors.

As shown in FIG. 4, in the learning, a large number of medical images obtained by full sampling are used as training images, and the learning is performed in a set of an image including noise (hereinafter referred to as an image with noise) obtained by under sampling in which sampling is reduced and the training images. The analysis unit 21 analyzes the noise pattern included in the noise image, and classifies the noise pattern into a plurality of patterns (1 to N). The analysis includes, for example, calculating characteristic values from the training images, and classifying the characteristic values into a plurality of classifications based on the characteristic values (including a vector or a matrix in addition to a numerical value). The characteristic values can be extracted using data obtained by quantifying the texture of the image itself by a gray level co-occurrence matrix (GLCM), or using spatial data other than the image space obtained by performing Fourier transform, Wavelet transform, or discrete cosine transform on the image. A plurality of characteristic values can also be classified in combination. Details of the analysis method will be described later.

After the image is classified as described above, the learning is performed in the learning data set of the training images and the noise image for each noise pattern. A patch image is cut out from the learning data set, the learning is executed in tens of thousands of image sets or more, and the processor for each pattern is created.

In the classification, not only the characteristic values extracted from the image or the transformed image but also information on an imaging condition when acquiring the image, for example, an imaging parameter such as a measurement matrix size, may also be included in an element during classification.

When the measurement matrix size is added as the element of the classification, the processor may also be created for each measurement matrix by performing the learning for each measurement matrix size. Alternatively, by adjusting the kernel size and the kernel coefficient of the processor learned using the image data set of a predetermined measurement matrix size, a processor for the image whose measurement matrix size is different from the image used for the learning data set may also be generated.

[Noise and Artifact Removal Processing]

Figure 5:
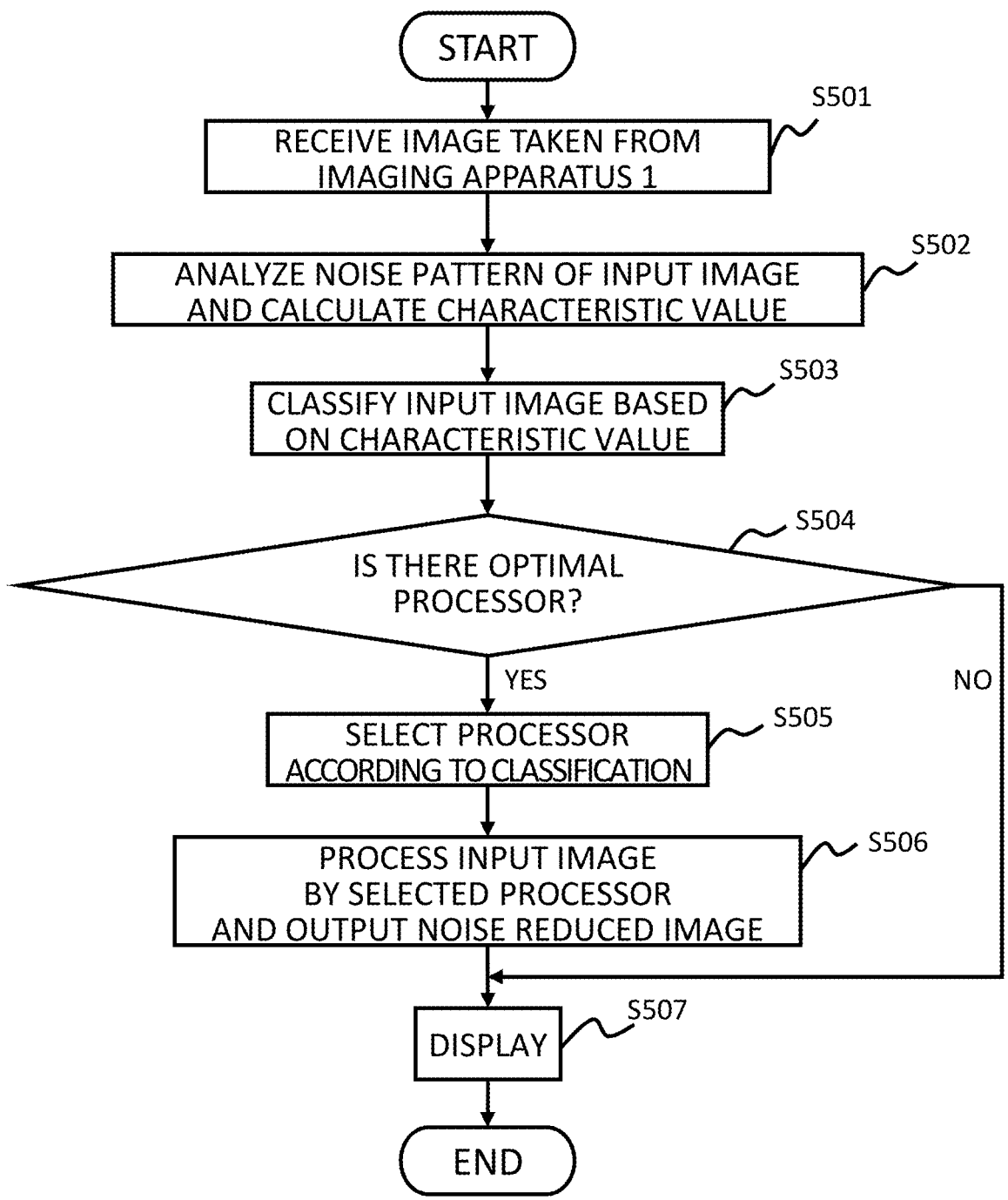
FIG. 5 is a diagram showing a flow of a processing using the medical image processing device according to the embodiment.

After the learning of the plurality of processors corresponding to the noise patterns is performed, the medical image processing device 2 performs a noise processing on an actually input medical image. An outline of the noise processing is shown in FIG. 5. As shown in the drawing, when the image processing device 2 inputs the medical image (S501), the analysis unit 21 analyzes the noise of the input image (S502), and classifies the input image into any of a plurality of predetermined noise patterns based on the analysis result (S503). The analysis and the classification performed by the analysis unit 21 are the same as the analysis and the classification performed when the learning model is created, and are performed based on the characteristic values extracted from characteristics of the image.

The processor selection unit 22 selects the processor 23 corresponding to the noise pattern into which the input image is classified (S505). As the analysis result of the analysis unit 21, for example, when the characteristic value is at a boundary of the plurality of patterns or the characteristic value is a value between a plurality of measurement matrix sizes used for the classification, a plurality of patterns of processors may be used in combination, or a processor corresponding to a group in which a distance between the characteristic value and a median value in a classified group is the closest may be used.

In addition, as the analysis result of the analysis unit 21, for example, when appropriate classification cannot be performed, for example, when a noise amount greatly exceeds a range of the noise amount of the learning data used for the learning of the processors 23 or an artifact is large and does not fit to the classification, the processor selection unit 22 may determine that there is no optimal processor (S504), and may display absence of the optimal processor on the display device 3 (S507), so that an inappropriate processing can be prevented in advance.

The processor 23 selected by the processor selection unit 22 executes an image quality improvement processing on the input image (S506). In the processing by the CNN, reliability of the processing can be obtained, for example, as probability of an output result, and thus the reliability may be determined from the probability or the like and displayed on the display device 3 (S507).

Figure 6:
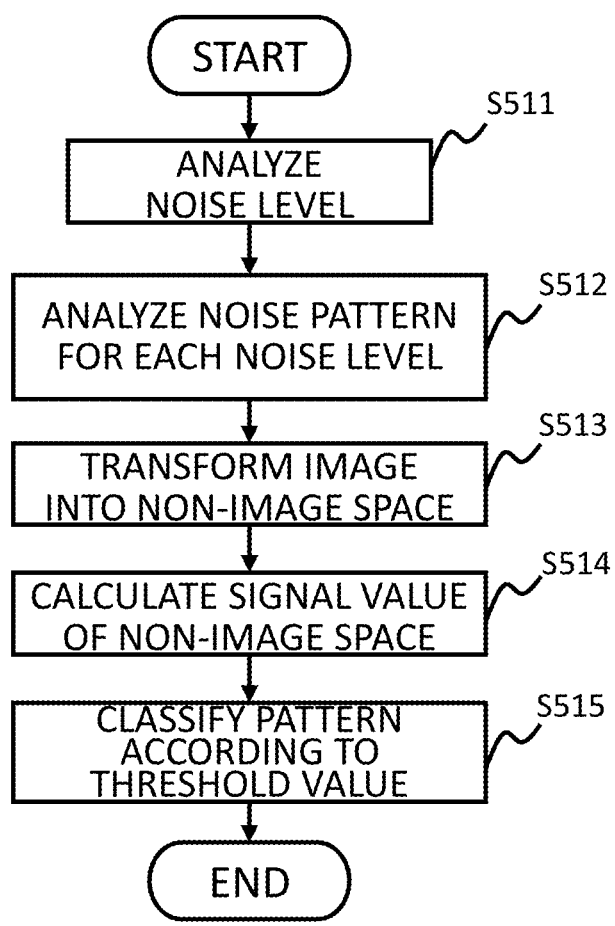
FIG. 6 is a diagram showing a flow of a noise processing according to the embodiment.

Next, a specific processing of the analysis unit 21 will be described. Here, as an example of images having different noise patterns, an example will be described in which the images are acquired by the MRI apparatus and the characteristic values are calculated for two images having different measurement matrix sizes. FIG. 6 shows a flow of an analysis processing.

The noise analysis unit 21 analyzes the pattern of the noise in the input image as the noise characteristic.

A magnitude of the noise (noise level) can be calculated from, for example, a histogram of the image with noise. The analysis unit 21 calculates the noise level from the histogram, sets a threshold value to the histogram, and performs the classification (rough classification) based on the magnitude of the noise (S511).

Next, analysis of the noise pattern is performed for each group having different noise levels (S512).

Figure 7A:
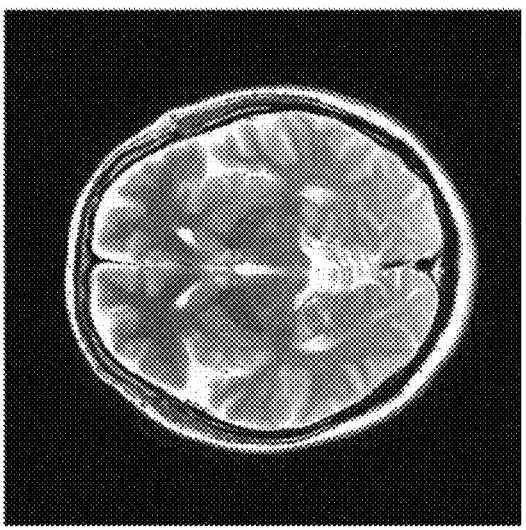
FIGS. 7A and 7B are diagrams showing examples of images having different noise patterns.
Figure 7A:
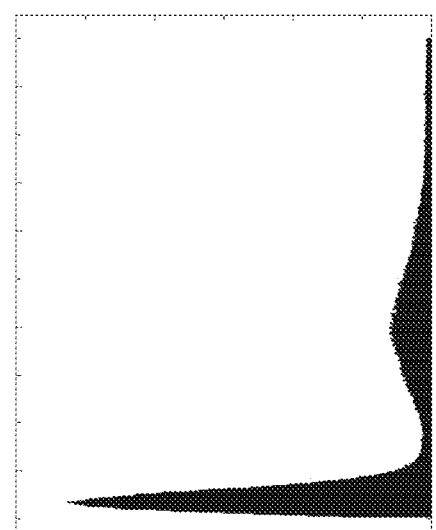
Figure 7B:
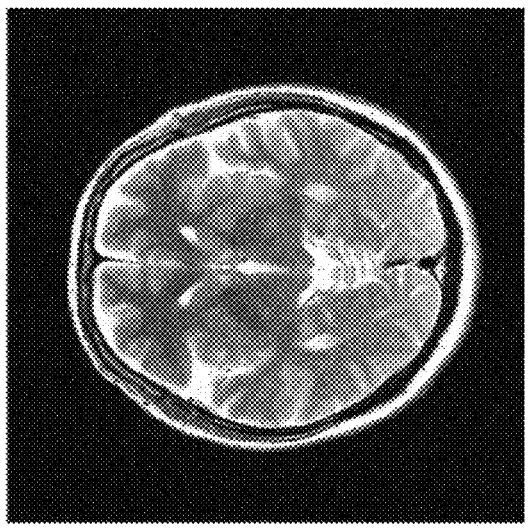
Figure 7B:
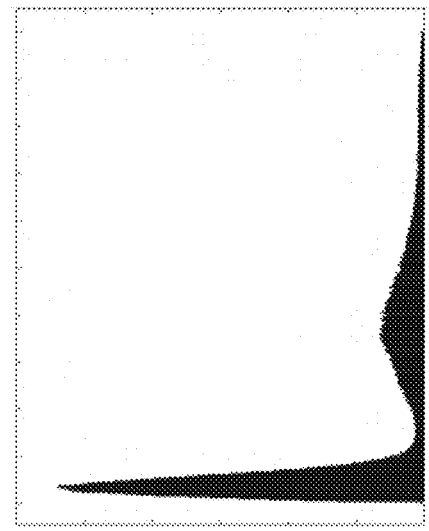

FIGS. 7A and 7B show examples of the images having the different noise patterns. FIGS. 7A and 7B show MR images acquired with different measurement matrix sizes. FIG. 7A shows an image in which the measurement matrix size is 512×512, FIG. 7B shows an image in which the matrix size is 256×256, and a reconstruction matrix shows a case of aligning to 512×512. When viewed in histograms of entire images, the same distribution is shown in FIGS. 7A and 7B, and the noise levels appear to be the same.

Figure 8A:
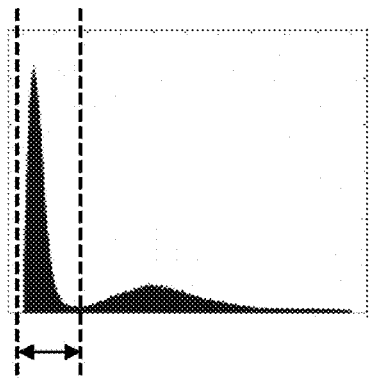
FIGS. 8A and 8B are diagrams showing images obtained by extracting a region of a range in a histogram.
Figure 8A:
Figure 8A:
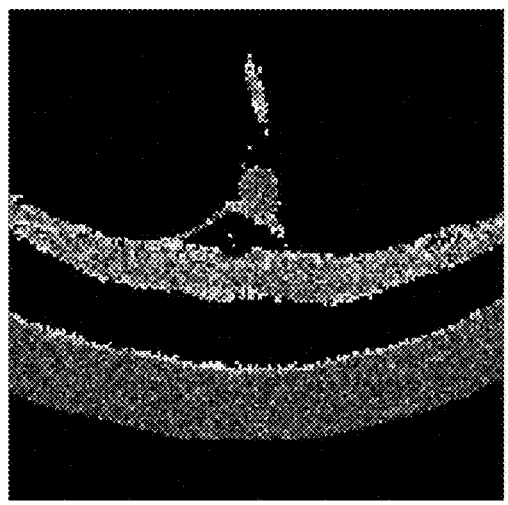
Figure 8B:
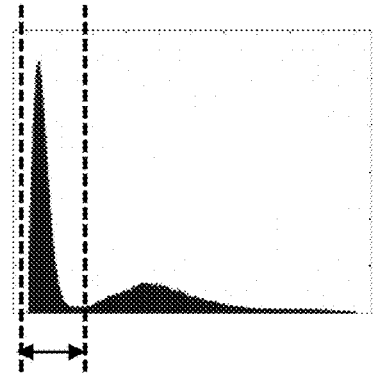
Figure 8B:
Figure 8B:
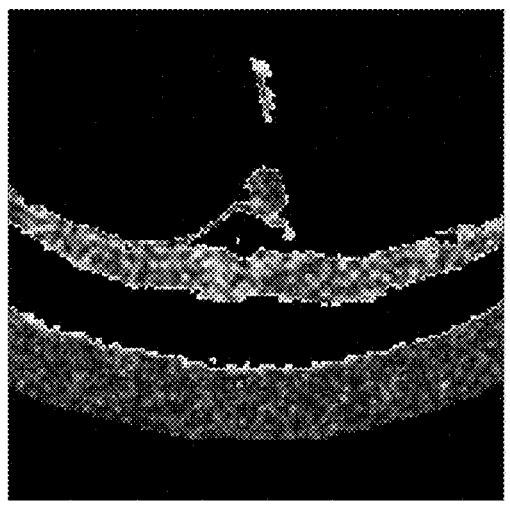

FIGS. 8A and 8B show images obtained by extracting regions of predetermined ranges in the histograms of the images of FIGS. 7A and 7B. In FIG. 8A, the measurement matrix size is 512×512, and in FIG. 8B, the measurement matrix size is 256×256. As can be seen from enlarged views, the patterns of the noises are different. Specifically, the pattern is rough in FIG. 8B as compared with the pattern in FIG. 8A.

In order to classify the patterns, the analysis unit 21 first transforms the images into data in the space other than the image space (S513), and calculates the characteristic values from the characteristics of transformed spatial data (S514).

Figure 9B:
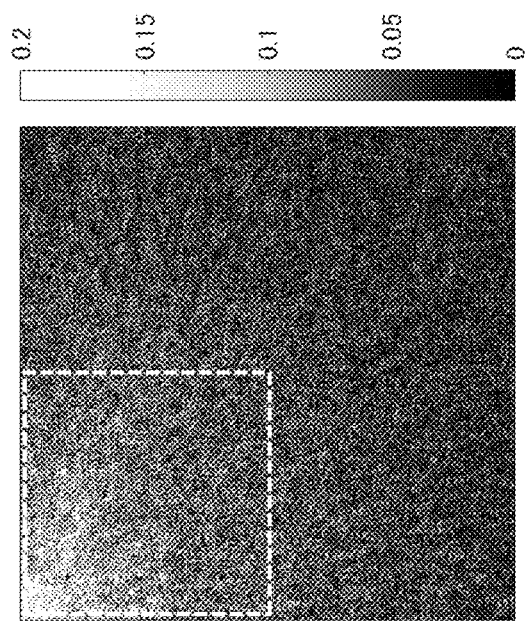
FIGS. 9A and 9B are diagrams showing data obtained by transforming the images having different noise patterns into spatial data other than an image space.
Figure 9A:
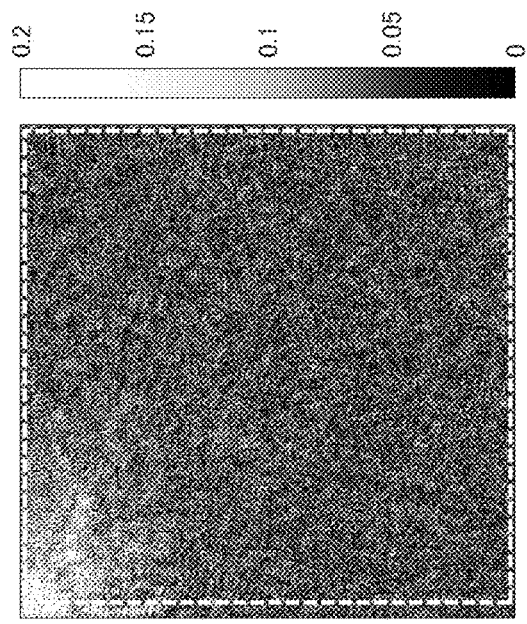

FIGS. 9A and 9B show the data obtained by transforming the images with noise into the spatial data other than the image space for the images of FIGS. 7A and 7B. Here, data (frequency spatial data) after the discrete cosine transform (DCT) is shown.

When pieces of data are compared with each other in the same spatial data, the characteristic of each piece of data is different according to the difference in the noise patterns (here, the difference in spatial distributions of the noises caused by the measurement matrix size). As compared with FIG. 9A, FIG. 9B shows that a value on a lower right side in the figure is small, which indicates that a high-frequency component included in the image with noise is small. This case indicates that the pattern of the noise is rough.

Therefore, in the present embodiment, first, the input image is subjected to the discrete cosine transform (S513). For the transformed data, as shown in FIGS. 9A and 9B, an average value is calculated for four regions of the transformed data (S514), and the pattern is classified by the threshold value (S515). Alternatively, a ratio of signal values of a plurality of regions may be used. For example, 0.5, 1, 1.5, or the like are set as threshold values of a certain ratio, and the pattern is classified into groups having ratios of less than 0.5, 0.5 to less than 1.0, 1.0 to less than 1.5, or 1.5 or more.

Figure 10A:
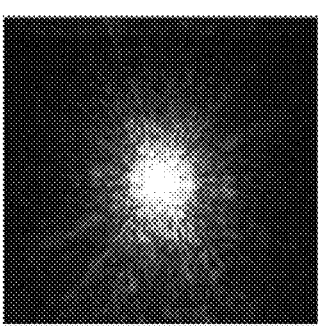
FIGS. 10A to 10D are diagrams of the images having different noise patterns corresponding to FIGS. 8A and 8B and 9A and 9B.
Figure 10A:
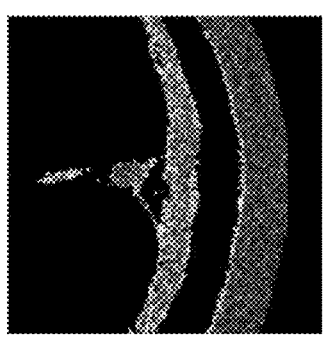
Figure 10A:
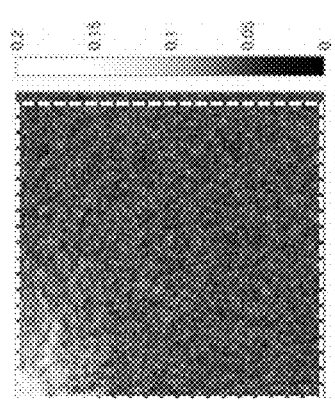
Figure 10B:
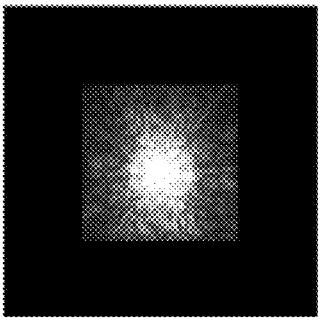
Figure 10B:
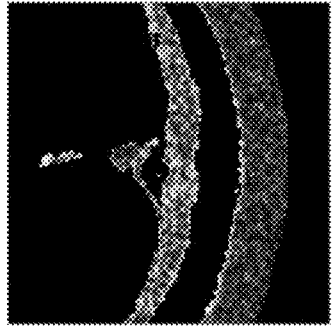
Figure 10B:
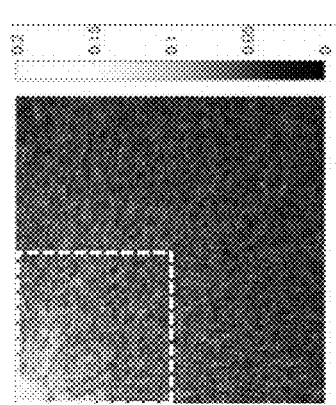
Figure 10C:
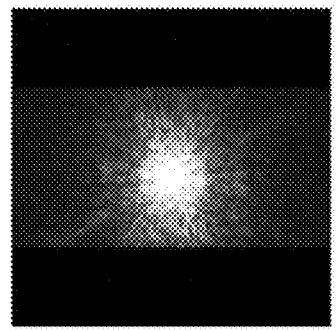
Figure 10C:
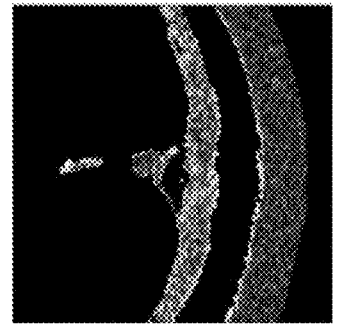
Figure 10C:
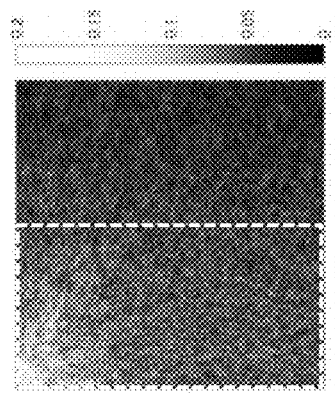
Figure 10D:
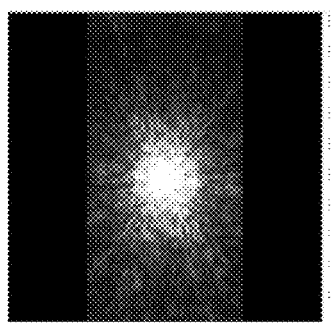
Figure 10D:
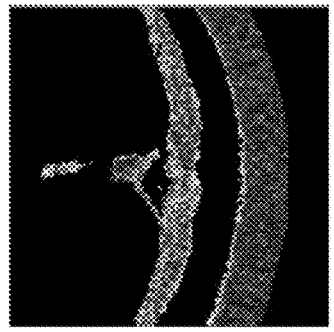
Figure 10D:
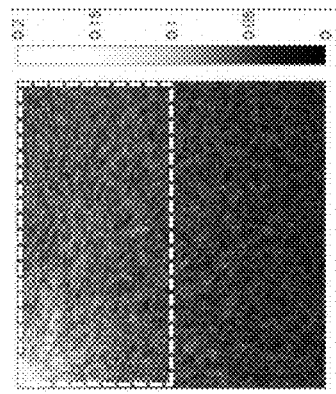

FIGS. 10A, 10B, 10C and 10D show cases where the measurement matrix is asymmetric (FIGS. 10A and 10B show the cases where the measurement matrixes shown in FIGS. 9A and 9B are 512×512 and 256×256). FIG. 10C shows the case where the measurement matrix size is 512×256 and FIG. 10D shows the case where the measurement matrix size 256×512. In FIG. 10C, the noise has a fine frequency in a vertical direction, and in FIG. 10D, the noise has a fine frequency in a horizontal direction, which can be seen from DCT results.

As described above, the example in which the difference in noise distributions due to the measurement matrix size is used as the pattern of the classification is described with reference to FIGS. 6 to 10D. Alternatively, the difference in the noise patterns other than the above can also be classified by using non-image spatial data suitable for classifying the pattern.

For example, the analysis unit 21 may use the Fourier transform or the Wavelet transform as transformation other than the discrete cosine transform (DCT). Further, the classification may be performed based on the characteristics of the image itself instead of transformation to the non-image spatial data. For example, texture analysis of the image is performed, the gray-level co-occurrence matrix (GLCM) or gray-level size zone matrix (GLZM) may be calculated, and an index of a decrease in uniformity due to the noise may be calculated as the characteristic value from the distribution. When the texture analysis of the image is performed, the input image may be displayed on the display device 3, and the user may instruct a region to be analyzed. Accordingly, calculation load by the analysis unit 21 can be reduced.

In addition, the classification may be performed based on information on the spatial distributions of signals from a living body received by a receiving coil. Even in a case of imaging the same site in the same examination, the spatial distributions of sensitivity differ depending on a size of a body of a patient. For example, in a case of imaging an abdomen of a patient having a large size, receiving sensitivity is likely to be low in a deep region of the abdomen. In addition, depending on an imaging site and a type of the receiving coil to be used, a region where the receiving sensitivity is locally low or a region where the receiving sensitivity is locally high may occur. For example, in imaging of a spine, a receiving sensitivity distribution differs between a case where the receiving coil is arranged only on a back side and a case where receiving coils are arranged on both back and abdomen sides. The spatial distribution of the noise also differs according to the receiving sensitivity distribution. The spatial distribution of the noise may be regarded as the noise pattern, and the image may be classified. In this case, a processor learned with the plurality of noise patterns, which are the spatial distributions of the noise, is prepared.

Further, for the image in which the above spatial distributions of the noise are classified as the noise patterns, the region to be analyzed can be specified or divided, a noise pattern other than the above (for example, a noise pattern based on the measurement matrix size, a noise pattern based on the receiving sensitivity distribution, and a signal pattern related to the noise) may be analyzed, a processor corresponding to the noise pattern may be selected for each region to perform the noise reduction processing.

Although the analysis of the noise pattern is basically performed automatically by the analysis unit 21, the user may be able to auxiliarily specify classification using a specific spatial distribution of the noise or what kind of the analysis of the noise pattern is to be performed. An example of a GUI that receives user designation is shown in FIG. 11.

Figure 11:
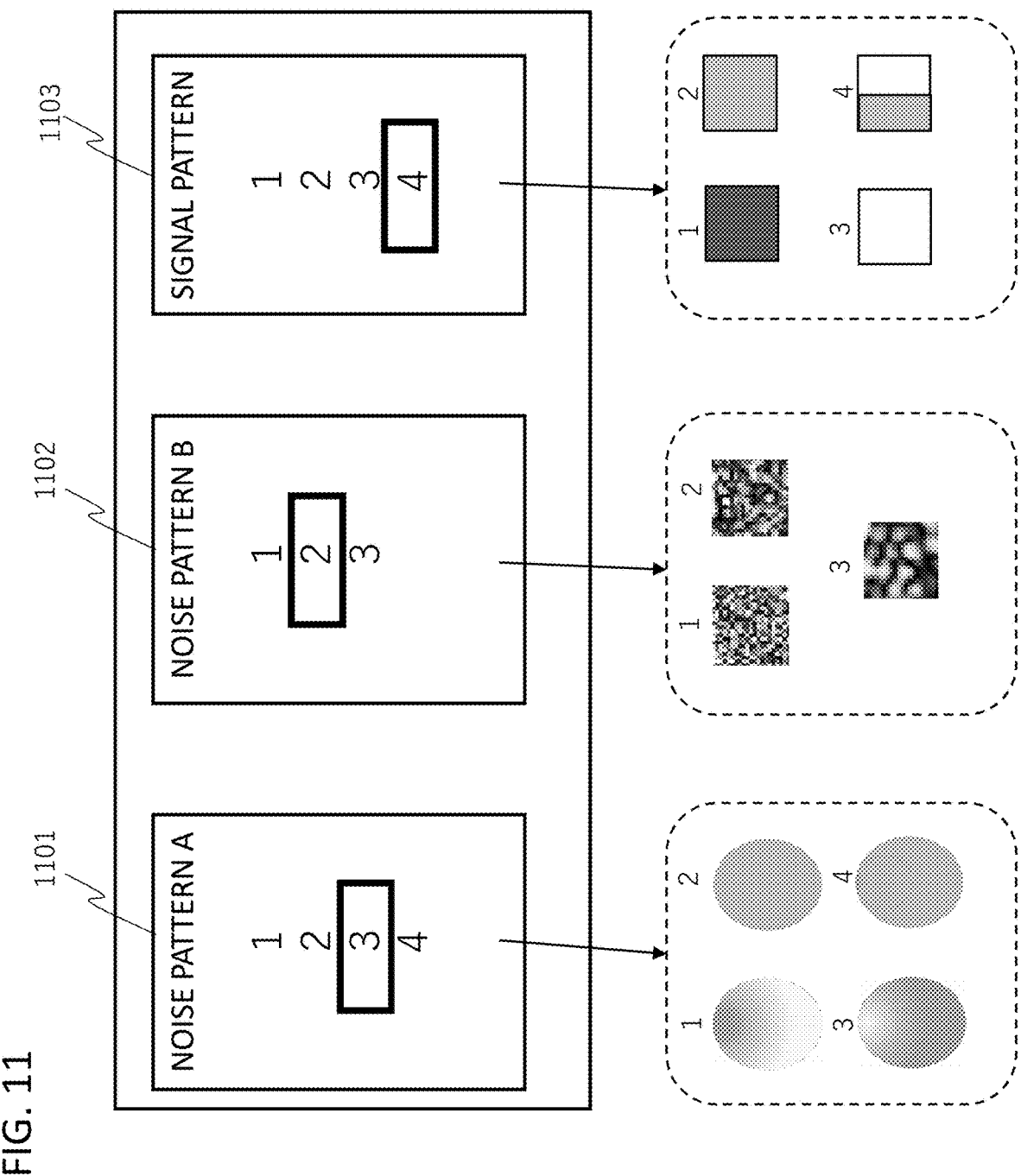
FIG. 11 is a diagram showing an example of a GUI that receives a user selection of a noise pattern to be analyzed.

In the example shown in FIG. 11, a GUI block 1101 for selecting the spatial distributions of the noise as the noise patterns, a GUI block 1102 for selecting the noise patterns by a measurement matrix, and a GUI block 1103 for selecting the noise patterns by the signal patterns are provided. A lower side of FIG. 11 is a diagram showing the noise patterns selected by the GUI blocks 1101 to 1103. In the GUI block 1101, for example, noise patterns 1 to 4 corresponding to the receiving sensitivity distribution can be selected for a cross section of a head, and the user selects a desired noise pattern (here, pattern 3 having high sensitivity at a center portion of the image) based on receiving sensitivity distribution information obtained in advance. In the GUI blocks 1102 and 1103, the noise patterns can be selected based on the measurement matrix size and the signal pattern for a region of a predetermined magnitude (a region of a part of a cross-sectional image).

By providing such a GUI, for example, the user can perform an appropriate adjustment or an additional processing with respect to a denoise processing that is automatically analyzed and performed by the analysis unit 21, and a degree of freedom of the user can be increased.

Although a specific content of the processing performed by the analysis unit 21 is described above, the analysis unit 21 may perform the classification based on not only the receiving sensitivity distribution but also information on spatial distributions of transmission sensitivity generated by a transmission RF coil 151.

Although the case of analyzing the noise patterns is described, as pattern analysis, characteristics of the artifact may be analyzed and classified accordingly.

For example, as the artifact of an MRI image, there is a line-shaped artifact caused by an electrical product such as a biological monitor arranged in the vicinity of the MRI apparatus. For an image including the artifact, the analysis may be performed by the Fourier transform, the Wavelet transform, the discrete cosine transform, the texture analysis, or the like.

Also, in the analysis of the artifact, the input image may be displayed on the display device 3, and the user may instruct the region to be analyzed. Accordingly, the calculation load by the analysis unit 21 can be reduced.

Alternatively, when the artifact is analyzed, a position and a width of a line may be further extracted and used as the characteristic values to perform the classification. In this case, when the processors 23 that differ depending on presence or absence of the artifact are created for each predetermined noise pattern (for example, measurement matrix size) as learned models, the classification may be performed without the analysis of the noise pattern.

Further, although the line-shaped artifact is described, other types of artifacts such as a ring artifact and a blood flow artifact may be similarly pattern-analyzed and classified.

Further, as the imaging parameter, for example, information on a slice thickness and a magnetic field strength may be used as information other than the measurement matrix size.

<Modifications>

Although the embodiment of the analysis methods by the analysis unit 21 is described above, these methods can be combined, thereby implementing a construction of an appropriate learning model and the image quality improvement processing using the learning model.

Figure 12A:
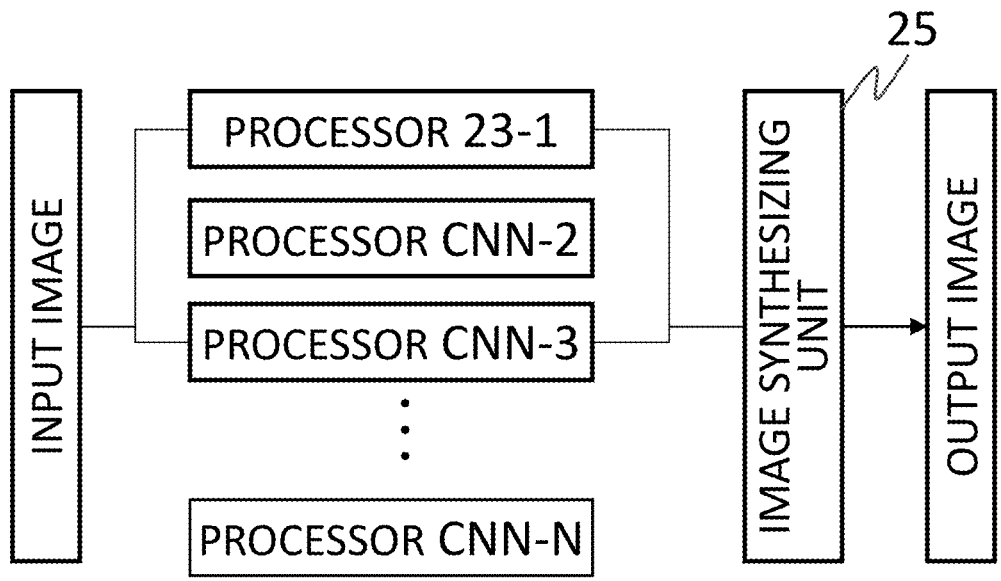
FIGS. 12A and 12B are diagrams showing modifications of a configuration of the processor.
Figure 12B:
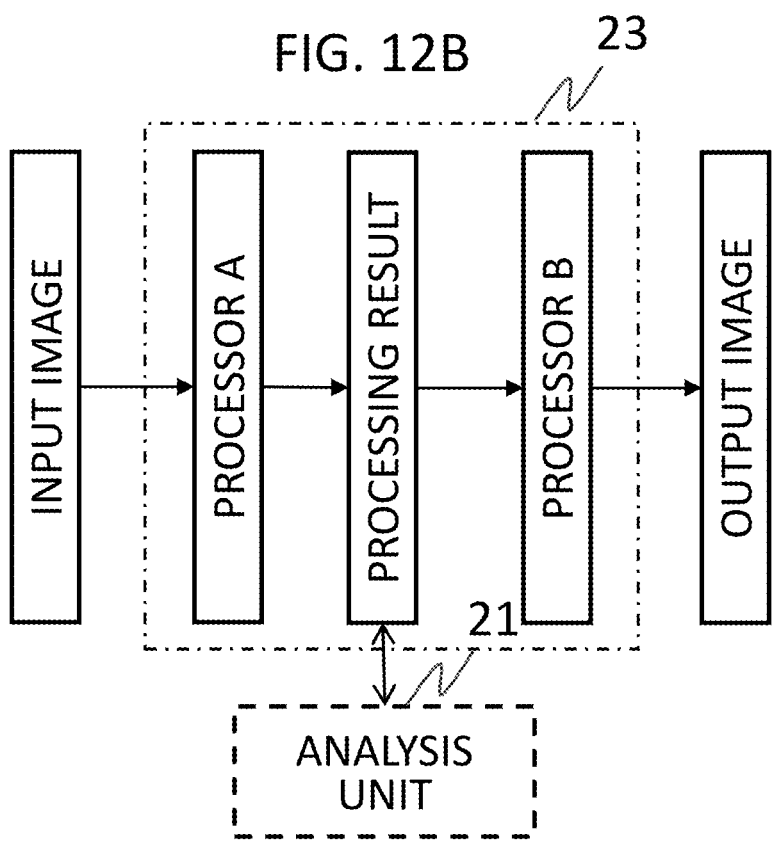

Further, instead of performing the processing with the single processor 23, application of the processors 23 may include performing the processing with the plurality of processors 23 at the same time as shown in FIG. 12A and synthesizing the results by an image synthesizing unit 25, and performing the processing by sequentially applying the plurality of processors as shown in FIG. 12B. For example, the processing may be performed by a processor for removing the artifact depending on the presence or absence of the artifact, and then the processing may be performed by a processor based on a noise pattern classification, or after a noise removal processing based on the measurement matrix size is performed, the processing may be performed by a processor selected according to the classification based on a noise pattern other than the above. When the processors are sequentially applied, the processing by the analysis unit 21 can be interposed as an intermediate processing.

<Embodiment of Medical Imaging Apparatus>

A configuration of an MRI apparatus will be described as an embodiment of a medical imaging apparatus.

Figure 13:
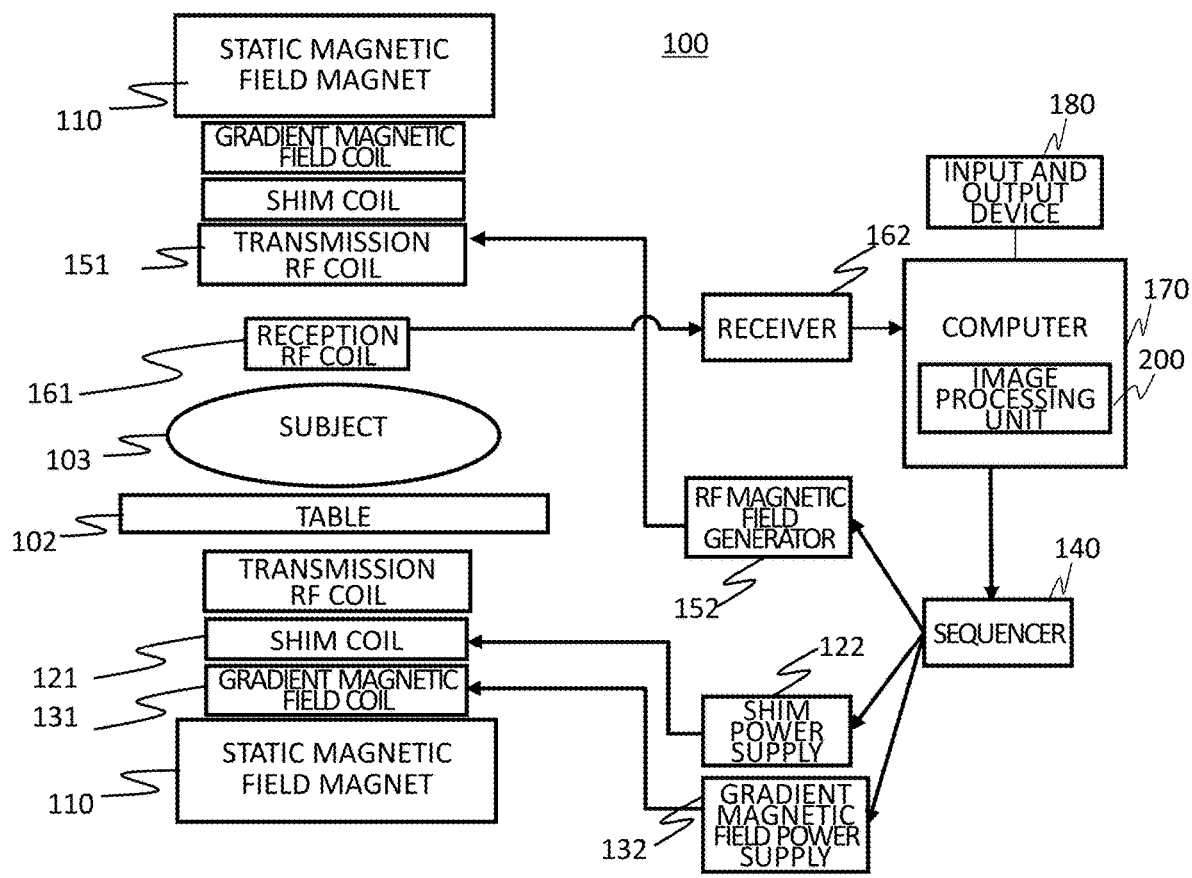
FIG. 13 is a diagram showing an MRI apparatus as an example of a medical imaging apparatus.

FIG. 13 is a diagram showing the embodiment of the MRI apparatus to which the invention is applied. An MRI apparatus 100 includes a static magnetic field magnet (static magnetic field generation unit) 110, a gradient magnetic field coil (gradient magnetic field generation unit) 131, the transmission RF coil 151, a receiving RF coil 161, a gradient magnetic field power supply 132, a shim coil 121, a shim power supply 122, a RF magnetic field generator 152, a receiver 162, a computer (image reconstruction unit) 170, and a sequencer 140. A reference numeral 102 denotes a table on which an imaging site of a subject 103 is placed in an imaging space.

The static magnetic field magnet 110 generates a static magnetic field in the imaging space. The static magnetic field magnet 110 may be a tunneling magnet that generates the static magnetic field in a horizontal direction by a solenoid coil, or may generate the static magnetic field in a vertical direction.

The gradient magnetic field coil 131 is connected to the gradient magnetic field power supply 132, and generates a gradient magnetic field in the imaging space. The shim coil 121 is connected to the shim power supply 122 and adjusts uniformity of the static magnetic field.

The transmission RF coil 151 is connected to the RF magnetic field generator 152, and emits (transmits) a RF magnetic field to the subject 103. A frequency of the RF magnetic field is set to a frequency that excites nuclear magnetism of a nucleus (proton or the like) of a nuclide of the subject 103 that is desired to be imaged. Any structure may be used as the transmission RF coil 151, and for example, a birdcage type RF coil may be used.

The receiving RF coil 161 is connected to the receiver 162 and receives a nuclear magnetic resonance signal from the subject 103. The receiving RF coil 161 is, for example, a multi-channel RF coil (array coil) including a plurality of coil units, and thus high-speed imaging can be obtained by a parallel imaging method.

The sequencer 140 transmits instructions to the gradient magnetic field power supply 132 and the RF magnetic field generator 152 to operate the gradient magnetic field power supply 132 and the RF magnetic field generator 152. An instruction is transmitted to the shim power supply 122 to correct the uniformity of the static magnetic field. The instruction is transmitted in accordance with an instruction from the computer 170. Further, the sequencer 140 sets a magnetic resonance frequency as a reference for detection in the receiver 162 according to the instruction from the computer 170. Specifically, during imaging, the gradient magnetic field and the RF magnetic field are irradiated from the gradient magnetic field coil 131 and the transmission RF coil 151 to the subject 103 at predetermined timings, respectively, in accordance with an instruction from the sequencer 140. The nuclear magnetic resonance signal generated by the subject 103 is detected by the receiving RF coil 161, and detected by the receiver 162. Accordingly, an imaging pulse sequence for implementing a predetermined imaging method is executed.

The computer 170 controls an overall operation of the MRI apparatus 100 and performs various types of signal processings. For example, the computer 170 transmits an instruction to the sequencer 140 such that each device operates at a timing and strength programmed in advance. When the parallel imaging is performed, phase encoding is thinned out every other line, execution time of the imaging pulse sequence is shortened, and the high-speed imaging is implemented.

In addition, the computer 170 receives the signal detected by the receiver 162 via an A/D conversion circuit (not shown), and performs the signal processings such as an image reconstruction. In a case of the high-speed imaging such as the parallel imaging, the image reconstruction is performed using a sensitivity map of an array coil, and calculation excluding folding after the image reconstruction is performed. Further, the computer 170 performs a processing such as correction including the noise reduction on a reconstructed image. These processings are executed by an image processing unit 200 constructed in the computer 170. In addition, the computer 170 is connected to an input and output device 180 including a display device for displaying a processing result and an input device for the user to input desired imaging conditions and the like.

A configuration of the image processing unit 200 is the same as that of the image processing device 2 shown in FIG. 1, the image reconstructed by the computer 170 is used as the input image, and the image quality improvement processing such as the noise reduction and artifact removal is executed. At this time, the analysis and the classification of the input image are performed using imaging parameters when the input image is taken as necessary.

The image subjected to the image quality improvement processing by the image processing unit 200 is displayed on the input and output device (display device). At this time, the image before the image quality improvement processing or the like may be juxtaposed and displayed, the reliability of the image quality improvement processing may be displayed, and thus the user can confirm whether the processing is appropriately performed.

According to the MRI apparatus of the present embodiment, the appropriate noise processing can be performed on various images acquired at different imaging conditions and different high-speed rates without performing an inappropriate noise processing.

What is claimed is:

1. A medical image processing device that inputs an image acquired by a medical imaging apparatus and outputs an image in which noise is reduced, the medical image processing device comprising:
    a plurality of processors for noise reduction;
    an analysis unit configured to analyze a pattern of a signal and noise of the input image and classify the input image; and
    a processor selection unit configured to select one or a plurality of processors from the plurality of processors based on a classification result of the analysis unit and activate the selected processor,
    wherein the analysis unit transforms the input image into frequency spatial data other than an image space, and classifies the input image using a spatial pattern of the frequency spatial data.

2. The medical image processing device according to claim 1, wherein the analysis unit transforms the input image into sparse spatial data, and classifies the input image using signal values of a plurality of regions of the sparse spatial data or a ratio thereof.

3. The medical image processing device according to claim 1, wherein
    the analysis unit classifies the input image based on a characteristic value calculated by texture analysis of the input image.

4. The medical image processing device according to claim 1, wherein
    the analysis unit classifies the input image based on a pattern of an artifact included in the input image.

5. The medical image processing device according to claim 4, wherein
    the analysis unit classifies the input image based on presence or absence of a line-shaped artifact included in the input image and a line pattern.

6. The medical image processing device according to claim 1, wherein
    the input image is an image acquired by a magnetic resonance imaging apparatus, and is classified by information on a spatial distribution of a signal from a living body received by a receiving coil.

7. The medical image processing device according to claim 1, wherein
    the analysis unit acquires an imaging parameter together with the input image when the input image is acquired, and classifies the input image using the imaging parameter.

8. The medical image processing device according to claim 7, wherein
    the input image is an image acquired by a magnetic resonance imaging apparatus, and the imaging parameter includes a measurement matrix size and a reconstruction matrix size.

9. A medical imaging apparatus comprising:
    an imaging unit configured to take an image of a subject and acquire a medical image; and
    an image processing unit configured to process the medical image acquired by the imaging unit, wherein
    the image processing unit includes the medical image processing device according to claim 1.

10. A noise reduction method for reducing noise included in an image acquired by a medical imaging apparatus, the method comprising:
    analyzing a pattern of the noise of the image and classifying an input image;
    selecting a predetermined processor from a plurality of processors for noise reduction prepared for each classification based on a classification result of the classification; and
    executing a noise reduction processing of the input image by the selected processor, wherein
    the classification uses a high-speed imaging condition when the input image is acquired together with the analysis results in the classification of the input image.

11. The noise reduction method according to claim 10, wherein
    the analysis of the pattern of the noise includes at least one of (i) histogram analysis of the image, (ii) texture analysis of the image, and (iii) analysis of data after a frequency spatial transformation or a sparse spatial transformation, and the input image is classified based on one or a plurality of analysis results.

12. A noise reduction method for reducing noise included in an image acquired by a medical imaging apparatus, the method comprising:
    analyzing a pattern of the noise of the image and classifying an input image;
    selecting a predetermined processor from a plurality of processors for noise reduction prepared for each classification based on a classification result of the classification;
    executing a noise reduction processing of the input image by the selected processor;
    selecting no processor after the classification; and
    displaying on a display device to select no processor.

* * * * *